(12) United States Patent
Mukhopadhyay et al.

(10) Patent No.: US 9,764,015 B2
(45) Date of Patent: Sep. 19, 2017

(54) HEMOGLOBIN RECEPTOR AS NOVEL VACCINE FOR LEISHMANIASIS

(71) Applicants: NATIONAL INSTITUTE OF IMMUNOLOGY, New Delhi (IN); INDIAN INSTITUTE OF CHEMICAL BIOLOGY, Kolkata (IN)

(72) Inventors: Amitabha Mukhopadhyay, New Delhi (IN); Syamal Roy, Kolkata (IN); Deepika Gupta, New Delhi (IN); Rajan Guha, Kolkata (IN); Ruchir Rastogi, New Delhi (IN)

(73) Assignees: National Institute of Immunology, New Delhi (IN); Indian Institute of Chemical Biology, Kolkata (IN)

( * ) Notice: Subject to any disclaimer, the term of this patent is extended or adjusted under 35 U.S.C. 154(b) by 0 days.

(21) Appl. No.: 14/648,538

(22) PCT Filed: Apr. 11, 2014

(86) PCT No.: PCT/IN2014/000231
§ 371 (c)(1),
(2) Date: May 29, 2015

(87) PCT Pub. No.: WO2014/184797
PCT Pub. Date: Nov. 20, 2014

(65) Prior Publication Data
US 2015/0306195 A1  Oct. 29, 2015

(30) Foreign Application Priority Data

May 15, 2013  (IN) .......................... 1449/DEL/2013

(51) Int. Cl.
| | |
|---|---|
| C07H 21/04 | (2006.01) |
| A61K 39/008 | (2006.01) |
| C07K 14/44 | (2006.01) |
| G01N 33/68 | (2006.01) |
| G01N 33/569 | (2006.01) |
| C07K 16/20 | (2006.01) |

(52) U.S. Cl.
CPC ............ *A61K 39/008* (2013.01); *C07K 14/44* (2013.01); *C07K 16/20* (2013.01); *G01N 33/56905* (2013.01); *G01N 33/6893* (2013.01); *G01N 2333/44* (2013.01); *G01N 2469/20* (2013.01)

(58) Field of Classification Search
CPC .................................................. A61K 39/008
See application file for complete search history.

(56) References Cited

U.S. PATENT DOCUMENTS

2015/0166562 A1* 6/2015 Fournier .............. A61K 31/445
514/302

OTHER PUBLICATIONS

G. Krishnamurthy et al: "Hemoglobin Receptor in Leishmania is a Hexokinase Located in the Flagellar Pocket", Journal of Biological Chemistry, vol. 280, No. 7, Feb. 18, 2005 (Feb. 18, 2005), pp. 5884-5891, XP055156113, ISSN: 0021-9258, DOI: 10.1074/jbe.M411845200 DOI: http://dx.doi.org/10.1074/jbe.M411845200.

Sudha B. Singh et al: "Rab5-Mediated Endosome-Endosome Fusion Regulates Hemoglobin Endocytosis in Leishmania donovani.", The Embo Journal, vol. 22, No. 21, Nov. 3, 2003 (Nov. 3, 2003), pp. 5712-5722, XP055155920, ISSN: 0261-4189.

N. Patel et al: "Leishmania Requires RAB7-Mediated Degradation of Endocytosed Hemoglobin for Their Growth", Proceedings of the National Academy of Sciences, vol. 105, No. 10, Mar. 11, 2008 (Mar. 11, 2008), pp. 3980-3985, XP055156248, ISSN: DOI: http://dx.doi.org/10.1073/pnas.0800404105.

Agarwal Shrui et al: "Clathrin-Mediated Hemoglobin Endocytosis is Essential for Survival of Leishmania", Biochimica Et Biophysica Acta. Molecular Cell Research, Elsevier Science Publishers, Amsterdam, NL, vol. 1833, No. 5, Jan. 14, 2013 (Jan. 14, 2013), pp. 1065-1077, XP029003831, ISSN: 0167-4889, DOI: 10.1016/J.BBAMCR.2013.01.006 DOI: http://dx.doi.org/10.1016/j.bbamer.2013.01.006.

Gleb Pishchany et al: "Taste for Blood: Hemoglobin as a Nutrient Source for Pathogens", PLOS Pathogens, Mar. 1, 2012 (Mar. 1, 2012), p. e1002535, XP55135925, DOI: 10.1371/Journal Retrieved from the Internet: URL:http://www.plospathogens.org/article/fetchObject.action?uri=infodoi/10.1371/journal.ppat.1002535&representation=PDF [retrieved on Dec. 1, 2014] DOI: http://dx.doi.org/10.1371/journal.

Guha Rajan et al: "Vaccination with Leishmania Hemoglobin Receptor-Encoding DNA Protects Against Visceral Leishmaniasis", Science Translation Medicine, American Association for the Advancement of Science, US, vol. 5, No. 202, Sep. 1, 2013 (Sep. 1, 2013), pp. 54-64, XP009181500, ISSN: 1946-6234.

* cited by examiner

*Primary Examiner* — Albert Navarro
(74) *Attorney, Agent, or Firm* — Ladas & Parry LLP

(57) ABSTRACT

The present invention in general relates Hemoglobin receptor or its part as a novel vaccine candidate against Leishmaniasis. Specifically, the present invention envisages HbR DNA for eliciting immune response in a mammal against Leishmaniasis. Additional aspect of the present invention is related to a vaccine composition for inducing immune response against Leishmaniasis in mammals. In a preferred aspect, the present invention relates to use of HbR-polypeptide as marker for diagnosis of *Leishmania* in kala-azar patients.

3 Claims, 14 Drawing Sheets c.

Sequence ID Number 1: Full length Hemoglobin receptor DNA sequence (HbR-FL):

```
atggccacccgcgtgaacaacctcctgagccacatcgctctccgcgactcggatagcgag
gagatgcgctacatcaagcagcgcctcgcgctcgcctccctcgccacccagttcaccatg
tcctcggagaagatgaagcagctcaccatgtacatgatccacgagatggtggagggtctt
gagggccgcccgagcaccgtgcgcatgctgccgtccttcgtgtacacgtccgacccggcc
aaggccaccggtgtgtactacgcgctcgacctcggcggcacgaacttccgcgtgttgcgt
gtgagcctgcgcggcggcaaggtggacgaccgcaccgactcgaagttcgtgatcccgaag
agtgccctggttggcgatgccacggacctgttcgacttcattgcgcagagcgtgaagaag
atgatgtcggagaacgcccccgacgacctggagaagcgcgtgccgctggggttcaccttc
tccttccggtggaccagaaggccgtcaacaagggactgctgatcaagtggacaaagggc
ttctcgacgaagaacgtggagggcaacgatgtggtggagctgctgcaggcgtcgctgcgc
cgcgtgcgcgtcaacgtgaacgtcgtggcgctctgcaacgacaccgtcggcacgctggtg
gcccgctacttcgtggacacggacgtgcaggtgggcgtcatcatcggcaccggctccaac
gcctgctactttgagcgcgcctcggccgttacgaaggaccccgccgtgtctgcccgcggc
aacgccgtcacgccgatcaacatggagtgcggtaacttcgactccaagtacaagtacgcg
ctgcccatcaccgtgtacgatgatgagatggacgcgatcacccccaaccgcgagaaccag
cgccaagagaagctcgtctccggcatgtacctgggtgagatctctcgccgcttgatcgtg
cacctggcgcagctcggctgcctgccccgcggctggtggatggcctgtgcaggccgtgg
gcgttcgagagtaagcacatgggtatgatcgccgccgatcagatgcccggcctgcagttc
acccgcgagctcatcaagcgcatcgctggtgtggatgtgactgatatgtccgacctgcac
acgattcgtgagacctgctgcctggtgcgtaaccgcgccgctcagcagggcgctgtcttc
acggctgctccgatgctcaagacccgcacgcagggtctcgccaccgtcgccgtcgacggc
tccgtgtacgagaagacgccgtccttccagcgcctgtaccaggagtgcataacgagcatc
ctcggaagcacgtcgaacgtgaaggtggtgctgcagaaggacggtagcggtgtcggcgcc
gcgatgatctgcgcgctggccgtcaacaagaagtag
```

Sequence ID Number 2: N-terminal Hemoglobin receptor DNA sequence (HbR-N):

```
atggccacccgcgtgaacaacctcctgagccacatcgctctccgcgactcggatagcgag
gagatgcgctacatcaagcagcgcctcgcgctcgcctccctcgccacccagttcaccatg
tcctcggagaagatgaagcagctcaccatgtacatgatccacgagatggtggagggtctt
gagggccgcccgagcaccgtgcgcatgctgccgtccttcgtgtacacgtccgacccggcc
aaggccaccggtgtgtactacgcgctcgacctcggcggcacgaacttccgcgtgttgcgt
gtgagcctgcgcggcggcaaggtggacgaccgcaccgactcgaagttcgtgatcccgaag
agtgccctggttggcgat
```

Sequence ID Number 3: Full length Hemoglobin receptor protein sequence (HbR-FL):

```
MATRVNNLLSHIALRDSDSEEMRYIKQRLALASLATQFTMSSEKMKQLTMYMIHEMVEGLEGRPSTVRMLPSFVY
TSDPAKATGVYYALDLGGTNFRVLRVSLRGGKVDDRTDSKFVIPKSALVGDATDLFDFIAQSVKKMMSENAPDDL
EKRVPLGFTFSFPVDQKAVNKGLLIKWTKGFSTKNVEGNDVVELLQASLRRVRVNVNVVALCNDTVGTLVARYFV
DTDVQVGVIIGTGSNACYFERASAVTKDPAVSARGNAVTPINMECGNFDSKYKYALPITVYDDEMDAITPNRENQ
RQEKLVSGMYLGEISRRLIVHLAQLGCLPRGLVDGLCRPWAFESKHMGMIAADQMPGLQFTRELIKRIAGVDVTM
SDLHTIRETCCLVRNRAAQQGAVFTAAPMLKTRTQGLATVAVDGSVYEKTPSFQRLYQECITSILGSTSNVKVVL
QKDGSGVGAAMICALAVNKK
```

FIG. 9

SEQUENCE LISTING

```
<160> NUMBER OF SEQ ID NOS: 3

<210> SEQ ID NO 1
<211> LENGTH: 1416
<212> TYPE: DNA
<213> ORGANISM: Leishmania

<400> SEQUENCE: 1
atggccaccc gcgtgaacaa cctcctgagc cacatcgctc tccgcgactc ggatagcgag      60
gagatgcgct acatcaagca gcgcctcgcg ctcgcctccc tcgccaccca gttcaccatg     120
tcctcggaga agatgaagca gctcaccatg tacatgatcc acgagatggt ggagggtctt     180
gagggccgcc cgagcaccgt gcgcatgctg ccgtccttcg tgtacacgtc cgacccggcc     240
aaggccaccg gtgtgtacta cgcgctcgac ctcggcggca cgaacttccg cgtgttgcgt     300
gtgagcctgc gcggcggcaa ggtggacgac cgcaccgact cgaagttcgt gatcccgaag     360
agtgccctgc ttggcgatgc cacggacctg ttcgacttca ttgcgcagag cgtgaagaag     420
atgatgtcgg agaacgcccc cgacgacctg gagaagcgcg tgccgctggg gttcaccttc     480
```

-continued

```
tccttcccgg tggaccagaa ggccgtcaac aagggactgc tgatcaagtg gacaaagggc      540
ttctcgacga agaacgtgga gggcaacgat gtggtggagc tgctgcaggc gtcgctgcgc      600
cgcgtgcgcg tcaacgtgaa cgtcgtggcg ctctgcaacg acaccgtcgg cacgctggtg      660
gcccgctact tcgtggacac ggacgtgcag gtgggcgtca tcatcggcac cggctccaac      720
gcctgctact tgagcgcgc ctcggccgtt acgaaggacc ccgccgtgtc tgcccgcggc        780
aacgccgtca cgccgatcaa catggagtgc ggtaacttcg actccaagta caagtacgcg      840
ctgcccatca ccgtgtacga tgatgagatg gacgcgatca ccccaaccg cgagaaccag       900 cgccaagaga agctcgtctc cggcatgtac ctgggtgaga tctctcgccg cttgatcgtg      960
cacctggcgc agctcggctg cctgccccgc gggctggtgg atggcctgtg caggccgtgg     1020
gcgttcgaga gtaagcacat gggtatgatc gccgccgatc agatgcccgg cctgcagttc     1080
acccgcgagc tcatcaagcg catcgctggt gtggatgtga ctgatatgtc cgacctgcac     1140
acgattcgtg agacctgctg cctggtgcgt aaccgcgccg ctcagcaggg cgctgtcttc     1200
acggctgctc cgatgctcaa gacccgcacg cagggtctcg ccaccgtcgc cgtcgacggc     1260
tccgtgtacg agaagacgcc gtccttccag cgcctgtacc aggagtgcat aacgagcatc     1320
ctcggaagca cgtcgaacgt gaaggtggtg ctgcagaagg acggtagcgg tgtcggcgcc     1380
gcgatgatct gcgcgctggc cgtcaacaag aagtag                                1416
```

<210> SEQ ID NO 2
<211> LENGTH: 378
<212> TYPE: DNA
<213> ORGANISM: Leishmania

<400> SEQUENCE: 2

```
atggccaccc gcgtgaacaa cctcctgagc cacatcgctc tccgcgactc ggatagcgag       60
gagatgcgct acatcaagca gcgcctcgcg ctcgcctccc tcgccacccca gttcaccatg      120 tcctcggaga agatgaagca gctcaccatg tacatgatcc acgagatggt ggagggtctt      180
gagggccgcc cgagcaccgt gcgcatgctg ccgtccttcg tgtacacgtc cgacccggcc      240
aaggccaccg gtgtgtacta cgcgctcgac ctcgcgggca cgaacttccg cgtgttgcgt      300
gtgagcctgc gcggcggcaa ggtggacgac cgcaccgact cgaagttcgt gatcccgaag      360
agtgccctgg ttggcgat                                                     378
```

<210> SEQ ID NO 3
<211> LENGTH: 469
<212> TYPE: PRT
<213> ORGANISM: Leishmania

<400> SEQUENCE: 3

```
Ala Thr Arg Val Asn Asn Leu Leu Ser His Ile Ala Leu Arg Asp Ser
1               5                   10                  15

Asp Ser Glu Glu Met Arg Tyr Ile Lys Gln Arg Leu Ala Leu Ala Ser
            20                  25                  30

Leu Ala Thr Gln Phe Thr Met Ser Ser Glu Lys Met Lys Gln Leu Thr
        35                  40                  45

Met Tyr Met Ile His Glu Met Val Glu Gly Leu Glu Gly Arg Pro Ser
    50                  55                  60

Thr Val Arg Met Leu Pro Ser Phe Val Tyr Thr Ser Asp Pro Ala Lys
65                  70                  75                  80

Ala Thr Gly Val Tyr Tyr Ala Leu Asp Leu Gly Gly Thr Asn Phe Arg
```

```
                        85                  90                  95
Val Leu Arg Val Ser Leu Arg Gly Gly Lys Val Asp Asp Arg Thr Asp
                100                 105                 110

Ser Lys Phe Val Ile Pro Lys Ser Ala Leu Val Gly Asp Ala Thr Asp
                115                 120                 125

Leu Phe Asp Phe Ile Ala Gln Ser Val Lys Lys Met Met Ser Glu Asn
130                 135                 140

Ala Pro Asp Asp Leu Glu Lys Arg Val Pro Leu Gly Phe Thr Phe Ser
145                 150                 155                 160

Phe Pro Val Asp Gln Lys Ala Val Asn Lys Gly Leu Leu Ile Lys Trp
                165                 170                 175

Thr Lys Gly Phe Ser Thr Lys Asn Val Glu Gly Asn Asp Val Val Glu
                180                 185                 190

Leu Leu Gln Ala Ser Leu Arg Arg Val Arg Val Asn Val Asn Val Val
                195                 200                 205

Ala Leu Cys Asn Asp Thr Val Gly Thr Leu Val Ala Arg Tyr Phe Val
                210                 215                 220

Asp Thr Asp Val Gln Val Gly Val Ile Ile Gly Thr Gly Ser Asn Ala
225                 230                 235                 240

Cys Tyr Phe Glu Arg Ala Ser Ala Val Thr Lys Asp Pro Ala Val Ser
                245                 250                 255

Ala Arg Gly Asn Ala Val Thr Pro Ile Asn Met Glu Cys Gly Asn Phe
                260                 265                 270

Asp Ser Lys Tyr Lys Tyr Ala Leu Pro Ile Thr Val Tyr Asp Asp Glu
                275                 280                 285

Met Asp Ala Ile Thr Pro Asn Arg Glu Asn Gln Arg Gln Glu Lys Leu
                290                 295                 300

Val Ser Gly Met Tyr Leu Gly Glu Ile Ser Arg Arg Leu Ile Val His
305                 310                 315                 320

Leu Ala Gln Leu Gly Cys Leu Pro Arg Gly Leu Val Asp Gly Leu Cys
                325                 330                 335

Arg Pro Trp Ala Phe Glu Ser Lys His Met Gly Met Ile Ala Ala Asp
                340                 345                 350

Gln Met Pro Gly Leu Gln Phe Thr Arg Glu Leu Ile Lys Arg Ile Ala
                355                 360                 365

Gly Val Asp Val Thr Met Ser Asp Leu His Thr Ile Arg Glu Thr Cys
370                 375                 380

Cys Leu Val Arg Asn Arg Ala Ala Gln Gln Gly Ala Val Phe Thr Ala
385                 390                 395                 400

Ala Pro Met Leu Lys Thr Arg Thr Gln Gly Leu Ala Thr Val Ala Val
                405                 410                 415

Asp Gly Ser Val Tyr Glu Lys Thr Pro Ser Phe Gln Arg Leu Tyr Gln
                420                 425                 430

Glu Cys Ile Thr Ser Ile Leu Gly Ser Thr Ser Asn Val Lys Val Val
                435                 440                 445

Leu Gln Lys Asp Gly Ser Gly Val Gly Ala Ala Met Ile Cys Ala Leu
                450                 455                 460

Ala Val Asn Lys Lys
465
```

HEMOGLOBIN RECEPTOR AS NOVEL VACCINE FOR LEISHMANIASIS

RELATED APPLICATION

This application is a national phase entry under 35 USC 371 of International Patent Application No PCT/IN2014/000231 filed on 11 Apr. 2014, which claims priority from India Patent Application No. 1449/DEL/2013 filed on 15 Mar. 2013, the diclosures of which are incorporated in their entirety by reference herein.

FIELD OF THE INVETION

The present invention in general relates to a *Leishmania* vaccine using active or inactive hemoglobin receptor either in DNA or protein forms for immunizing mammals.

BACKGROUND OF THE INVENTION

*Leishmania*, a protozoan pathogen, is the causative agent of various forms of leishmaniasis like cutaneous, mucocutaneous and visceral leishmaniasis; of which visceral Leishmaniasis is fatal (Kedzierski, et al., 2009). Leishmaniasis affects about 12 million people worldwide and 500,000 new cases are reported annually (WHO bulletin 2012). Drugs used for chemotherapy of leishmaniasis, such as antimonials, miltefosine, paromomycin and amphotericin B are very toxic, expensive and frequent resistance occurs against these drugs in endemic areas (Croft & Coombs, 2003). Moreover, no effective vaccine against leishmaniasis is available (WHO bulletin 2012). Now, it is well established that this disease is associated with the lack of Th1 response characterized by down-regulation of IL-12, IFN-γ while disease promoting Th2 cytokines like IL-4, IL-10 are up-regulated (Bacellar, et. al., 2000; Nylen & Sacks, 2007). Therefore, the major focus is to generate protective T-cell responses using appropriate antigen.

Thus, there is an immense requirement to develop an effective vaccine against leishmaniasis. Recently, considerable progress has been made and large numbers of *Leishmania* antigens have been tried as potential vaccine candidates including surface expressed antigens like gp63, gp46, PSA-2, receptors of activated C kinase (LACK), cysteine proteases (CP), kinetoplastid membrane protein-11 (KMP-11) etc with varied immune response and diverse species specific protection (Kedzierski, 2010; Singh & Sundar, 2012). However, vaccines protective against leishmaniasis are still not available. Therefore, there is need to identify a novel antigen which is physiologically important for the biology of the parasite.

In addition, no cost effective appropriate diagnostic procedure for detection of leishmaniasis is available. Microscopic examination of the Giemsa stained lesion biopsy smears, lymph node, bone marrow or spleen aspirates remain the standard test in areas of endemicity which require hospitalization. Moreover, owing to the low socio-economic status of the people who are largely affected by these diseases, the tests need to be simple and affordable. Molecular approaches like PCR for parasite detection, though specific, remain restricted to hospitals and research centers owing to its high cost (Franceschi et al., 2007). Recently, a specific immunochromatographic test has been developed based on k39 (a repetitive immunodominant epitope in a kinesin-related protein that is highly conserved among viserotropic *Leishmania* species) and sufficiently validated for field use (Hailu, 2002; Mathur et al., 2005). The test checks for the presence of anti-k39 IgG/M antibodies in serum and has shown excellent sensitivity (93-100%) and specificity (97-98%) in many VL-endemic countries (Alborzi et al., 2006; Pedras et al., 2008). However, there is a need to develop simple and cost effective diagnostic procedure against *Leishmania* infection.

*Leishmania* require heme from exogenous sources for growth due to lack of complete heme biosynthetic pathway (Sah, et. al., 2002). As heme, a critical prosthetic group required by the parasites for several metabolic pathways, thus, heme acquisition process in *Leishmania* could be a potential target (Kelly, et. al., 2003). *Leishmania* endocytosed hemoglobin (Hb) through a high affinity hemoglobin receptor (HbR) located on the cell surface (Sengupta, et. al., 1999) and internalized Hb is targeted to the lysosomal compartment where it is degraded to generate intracellular heme (Singh, et. al., 2003; Patel, et. al., 2008) which is used by *Leishmania* for their survival. This receptor is a surface localized hexokinase and N-terminal end of the receptor is extracellular hemoglobin binding region (Krishnamurthy, et. al., 2005). Thus, this molecule has dual roles; firstly, it acts as Hb receptor on cell surface and secondly, being hexokinase, it regulates glycolysis in parasites. Thus, HbR is bi-functional molecule performing two major functions in *Leishmania*. The present invention relates to active or inactive hemoglobin receptor or its parts either in DNA or protein forms as a novel immunogen for vaccine against leishmaniasis in mammals.

The present innovation demonstrates that HbR-DNA offers following major advantages over other vaccine candidates against VL.

a. HbR-DNA vaccination induces sterile protection against *Leishmania* infection in both mice and hamster.

b. It not only evokes protective Th1-response without any adjuvant but also suppresses disease promoting cytokines to confer sterile protection.

c. HbR is a bifunctional antigen possibly interferes with two major pathways in *Leishmania*.

d. Anti-HbR antibody inhibits both promastigote and amastigote growth, therefore, anti-HbR antibody present in vaccinated animals might kills extracellular parasites during infection process.

e. Successful protection of VL with vaccination of truncated HbR (HbR-N) indicates the feasibility of developing subunit vaccine of HbR against leishmaniasis.

f. HbR is conserved across Leishmania species and hence could also be potential candidate against different forms of leishmaniasis.

g. HbR protein or fragments thereof as marker for diagnosis of *Leishmania* in kala-azar patients.

SUMMARY OF THE INVENTION

One aspect of the present invention is related to a HbR DNA or its part for inducing sterile protection against virulent *Leishmania*, wherein said DNA comprises nucleotide sequence selected from the group consisting of: a) nucleotide sequence as set forth in any one of SEQ ID NO: 1 (HbR-FL), SEQ ID NO: 2 (HbR-N) or fragments thereof; b) a nucleotide sequence that encodes polypeptide having amino acid sequence as set forth in SEQ ID NO: 3.

In a preferred embodiment, the said DNA consists of nucleotide sequence as set forth in. SEQ ID NO: 2 (HbR-N).

A further aspect of the present invention is related to a polypeptide selected from the group consisting of: a) a polypeptide comprising the amino acid sequence as set forth in SEQ ID NO: 3; b) a polypeptide that is encoded by the nucleotide sequence as set forth in any of SEQ ID NO: 1 or SEQ ID NO: 2; and c) a polypeptide that is a fragment of SEQ ID NO: 3.

In a preferred embodiment, the said polypeptide is having the amino acid sequence as set forth in SEQ ID NO: 3.

Another aspect of the present invention is related to a recombinant DNA vector comprising the DNA as defined as hereinabove operably linked to a promoter.

Additional aspect of the present invention is related to a vaccine composition comprising any one of the polypeptide as defined hereinabove along with a pharmaceutically acceptable diluents or carrier wherein the said vaccine composition induces immune response against leishmaniasis in mammals.

In a preferred embodiment, the said vaccine composition comprises an adjuvant.

Another aspect of the present invention is related to a method for eliciting an immune response in mammals, comprising administering a vaccine composition as defined hereinabove to a mammal to be treated.

A further aspect of the present invention is related to use of the vaccine composition so obtained to induce immune response against leishmaniasis in mammals.

Another aspect of the present invention is related to a HbR-polypeptide as marker for diagnosis of *Leishmania* in kala-azar patients, wherein said polypeptide is selected from the group consisting of: a) a polypeptide comprising the amino acid sequence as set forth in SEQ ID NO: 3 or fragments thereof ; b) a polypeptide that is encoded by the nucleotide sequence as set forth in any of SEQ ID NO: 1 or fragments thereof.

A further aspect of the present invention is related to use of HbR-polypeptide as marker for diagnosis of *Leishmania* in kala-azar patients.

BRIEF DESCRIPTION OF THE DRAWINGS

The present invention and its various embodiments will now be described with the help of the accompanying drawings.

FIG. 3A. Splenic parasite burden in mice
FIG. 3B. Hepatic parasite burden in mice.
FIG. 3C. Splenic parasite burden in hamster.
FIG. 3D. Hepatic parasite burden in hamster.
FIG. 3E. Survival kinetics of vaccinated and parasite challenged hamsters during experimental period of 260 days post-infection.

FIG. 9. Sequence ID Number 1: Full length Hemoglobin receptor DNA sequence (HbR-FL): Sequence ID Number 2: N-terminal Hemoglobin receptor DNA sequence (HbR-N): Sequence ID Number 3: Full length Hemoglobin receptor protein sequence (HbR-FL):.

DETAILED DESCRIPTION OF THE INVENTION

Figure 1:
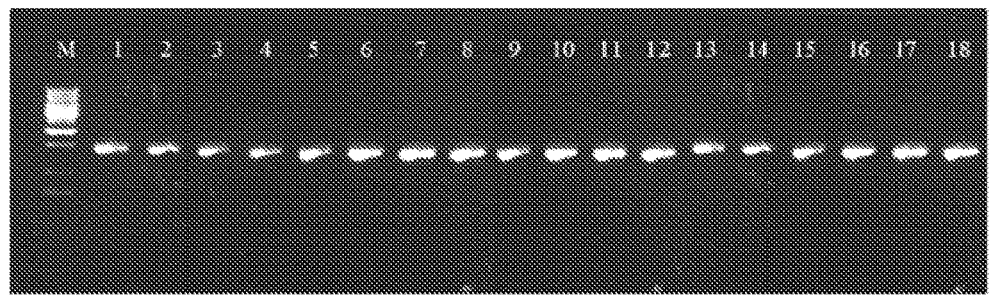
FIG. 1. PCR amplification of hemoglobin receptor from various. *Leishmania* species. Lane M, 1 kb DNA ladder (Promega) Lane 1, *L. amazonensis*; Lane 2, *L. amazonensis* var.7; Lane 3, *L. amazonensis* var.5; Lane 4, *L. infantum*; Lane 5, *L. infantum* var.2; Lane 6, *L. infantum* var.6; Lane 7, *L. donovani*; Lane 8, *L. major*; Lane 9, *L. major* var.1; Lane 10, *L. major* var. 4; Lane 11, *L. major* var. 4-2; Lane 12, *L. turanica*; Lane 13, *L. turanica* var.16; Lane14, *L.gerbilli*; Lane 15, *L. tropica*; Lane 16, *L. tropica* ver. 1; Lane 17, *L. tropica* ver. 7; Lane 18, *L. enrietti*.

The present invention is related to a HbR DNA for inducing sterile protection against virulent *Leishmania*, wherein said DNA comprises nucleotide sequence selected from the group consisting of: a) nucleotide sequence as set forth in any one of SEQ ID NO: 1 (HbR-FL), SEQ ID NO: 2 (HbR-N) or fragments thereof; b) a nucleotide sequence that encodes polypeptide having amino acid sequence as set forth in SEQ ID NO: 3.

In a preferred embodiment, the said DNA consists of nucleotide sequence as set forth in SEQ ID NO: 2 (HbR-N).

The present invention also relates to a polypeptide selected from the group consisting of: a) a polypeptide comprising the amino acid sequence as set forth in SEQ ID NO: 3; b) a polypeptide that is encoded by the nucleotide sequence as set forth in any of SEQ ID NO: 1 or SEQ ID NO: 2; and c) a polypeptide that is a fragment of SEQ ID NO: 3.

Preferably, the said polypeptide comprises the amino acid sequence as set forth in SEQ ID NO: 3.

The present invention also envisages a recombinant DNA vector comprising the DNA as defined hereinabove operably linked to a promoter.

The said promoter is selected from a group consisting of mammalian expression vectors but not limiting to CMV promoter.

Furthermore, the present invention is related to a vaccine composition comprising any one of the polypeptide as defined hereinabove along with a pharmaceutically acceptable diluents or carrier wherein the said vaccine composition induces immune response against Leishmaniasis in mammals.

The said diluents or carriers are selected from but not limited sterile saline.

In another preferred embodiment, the said mammals include but are not limited to mice, hamster, dogs, humans.

In a further preferred embodiment, the said vaccine optionally composition also comprises an adjuvant.

Preferably, the said adjuvant is selected from IL-12, GLA-SE (stable emulsion of monophosphoryl lipid A) and other related preparations.

The present invention is additionally related to a method for eliciting an immune response in mammals, comprising administering a vaccine composition as defined hereinabove to a mammal to be treated.

A further embodiment of the present invention is related to use of the vaccine composition so obtained to induce immune response against leishmaniasis in mammals.

In another embodiment, a HbR-polypeptide as marker for diagnosis of *Leishmania* in kala-azar patients, wherein said polypeptide is selected from the group consisting of: a) a polypeptide comprising the amino acid sequence as set forth in SEQ ID NO: 3 or fragments thereof; b) a polypeptide that is encoded by the nucleotide sequence as set forth in any of SEQ ID NO: 1 or fragments thereof is envisaged.

In a further embodiment, use of HbR-polypeptide as marker for diagnosis of *Leishmania* in kala-azar patients is enunciated.

In the present innovation, immunization of mammalian host with HbR-DNA or its part provides sterile protection against virulent *Leishmania donovani* infection in both BALB/c mice and hamster by inducing Th1 response.

Leishmaniasis is a complex diseases varying from cutaneous to visceral leishmaniasis, caused by diverse species of *Leishmania*. Ideally, an antigen use for developing effective vaccine against different forms of leishmaniasis should be present in different species of *Leishmania*. In the present innovation, HbR is found to be conserved among different species of *Leishmania*. Thus, the present invention is related to use HbR or its part as vaccine composition against different forms of leishmaniasis.

For the purpose of illustration, the invention will now be described non-limitatively in the following examples which are provided in order to demonstrate and further illustrate the preferred embodiments and aspects of the present invention.

EXAMPLES

The following Reagents and Chemicals were Used to Carry Out the Study as Set Forth in the Forthcoming Examples Medium RPMI-1640, M199, FCS (Sigma), Penicillin-Streptomycin solution (Invitrogen), Endo free Plasmid Mega/Giga Kit (Qiagen), anti-mouse CD4, CD8, CD3, TNF-α, IL-2 (BD Biosciences), anti-mouse IFN-γ (Biolegend), BD™ mouse Th1/Th2 cytokine kit II (BD Pharmingen) and BD™ CBA mouse Inflammatory kit (BD Pharmingen), Aqua Live/dead staining dye (Invitrogen) were used in the present study.

Animals and parasite

Four- to six-week-old BALB/c mice (Jackson Laboratory, Bar Harbour, Me., USA) and golden hamsters (*Mesocricetus auratus*), reared in pathogen free institute animal facilities, were used for experimental purposes with prior approval of the animal ethics committee of the Indian Institute of Chemical Biology (Kolkata, India). AG83 (MHOM/IN/83/AG83) strain of L. donovani was used for experimental purposes. Parasites were maintained in golden hamsters. Promastigotes obtained after transforming amastigotes from infected spleen were maintained in M199 (Sigma) supplemented with 100 U/ml penicillin, 100 µg/ml streptomycin, and 10% FCS. at 22° C.

Example 1

Presence of HbR in Different Species of *Leishmania*

Genomic DNA isolated from 18 different species and sub-strains of *Leishmania* were used. Full-length HbR were amplified from genomic DNA by RT-PCR from all 18 species and sub-strains of *Leishmania* using forward (5'-GTGGATCCATGGC CACCCGCGTGAAC-3') and reverse (5'-GTGAAT TCCTACTTCTTGTTGACGGCCA-3') primers designed against the start and stop codons of HbR by RT-PCR.

The results in the present innovation showed that full-length HbR from genomic DNAs of various strains of different *Leishmania* species namely, *L. amazonensi, L. infuntum, L. donovani, L. major, L. turanica, L. gerbilli, L. tropica, L. enrietti* are amplified (FIG. 1) and sequence comparison showed 95-100% identity.

Example 2

Evaluation of HbR as a Novel Vaccine Candidate against Leishmaniasis

Figure 2A:
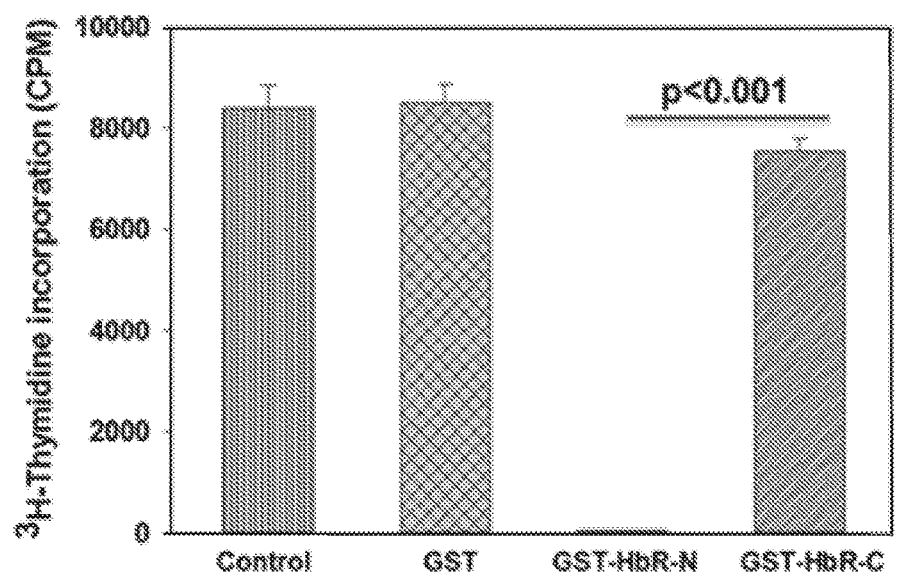
FIG. 2A. Promastigotes were incubated in presence equimolar amount of indicated proteins in M199 medium supplemented with [$^3$H]-thymidine for 12 h at 23° C. Cells were washed and the cell growth was measured by determining the amount of radioactivity incorporated by cells. Results are expressed as mean ±S.D. of three independent experiments.

HbR-FL, $HbR^{1-126}$ (HbR-N) and $HbR^{270-471}$ (HbR-C) were previously cloned, expressed as GST fusion proteins and specific antibodies were raised against HbR-N and HbR-C. Further characterization revealed that N-terminal of HbR, the $HbR^{1-126}$ (HbR-N) is extracellular hemoglobin binding domain and anti-HbR-N antibody or $HbR^{1-126}$ peptide specifically blocks hemoglobin uptake by *Leishmania* like HbR full-length (HbR-FL) protein (Krishnamurthy, et. al., 2005). Therefore, in the present investigation, effect of different fragments of HbR on the growth of *Leishmania* promastigotes were determine. Briefly, log phase promastigotes were washed, resuspended in M199 medium ($10^6$ cells/200 µl) containing equimolar, amount of GST-HbR-N or GST-HbR-C peptides (942 pmol/ml) along with $^3$H-thymidine (0.6 µCi/50 µl/well) and incubated for 12 h at 23° C. Cells were harvested using cell harvester and radioactivity incorporated by cells were determined. Our results show that HbR$^{1-126}$ (HbR-N) fragment specifically inhibits the complete growth of the parasites like HbR-FL protein (FIG. 2a).

Figure 2B:
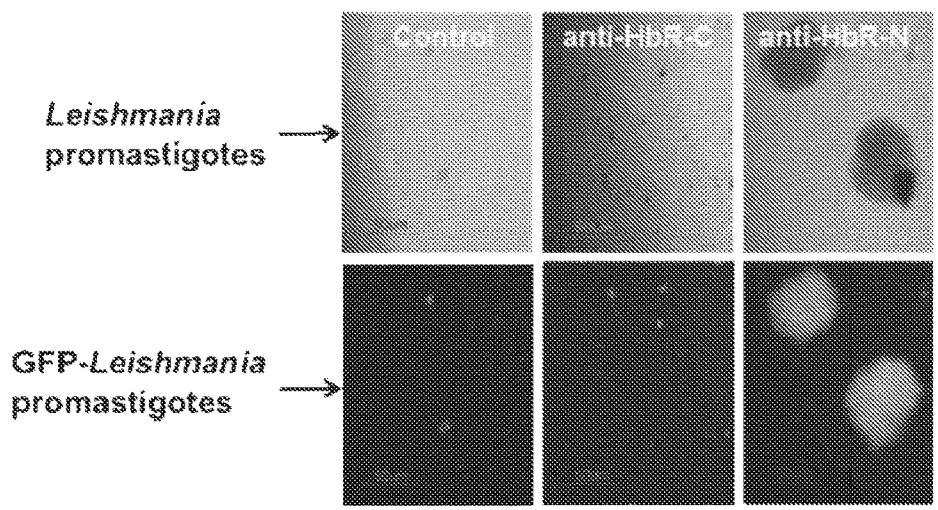
FIG. 2B. Fluorescent and phase images of HbR-GFP expressing *L. donovani* promastigotes (green) incubated in the presence of indicated antibodies. Pre-immune serum was used as control. Results are representative of three independent observations.

To determine effect of HbR-fragment-specific antibodies, log phase *Leishmania* promastigotes ($1\times10^7$ cells) were washed, resuspended in M199 medium containing anti-HbR-N, anti-HbR-C or pre-immune sera (1:100) and incubated for 10 min at 23° C. in 6-well tissue culture plates. Subsequently, the promastigotes were visualized using confocal microscopy. These results show that anti-HbR-N specifically induce the aggregation of the cells and thereby blocks the parasite growth (FIG. 2b). Therefore, in the present innovation, DNA constructs containing HbR-FL or HbR-N are used to evaluate the efficacy of HbR as potential vaccine candidate in experimental models visceral leishmaniasis.

Example 3

HbR Elicited Complete Protection against Visceral Leishmaniasis Both in Mice and Hamster BALB/c mice and hamsters models of visceral leishmaniasis are widely used to determine the efficacy of vaccine. Mice model is useful in understanding the immune dysfunction whereas golden hamster mimics the clinical features of visceral leishmaniasis and ultimately death. Therefore, in the present innovation, HbR-DNA as vaccine candidate was determined in both mice and hamster models of visceral leishmaniasis.

HbR-FL or HbR-N coding sequence was sub-cloned into Bam HI and Eco RI sites of mammalian expression vector (pcDNA3.1) downstream to the CMV promoter using respective primers.

```
HbR-FL:
Forward:
5'-GTGGATCCATGGCCACCCGCGTGAAC-3'

Reverse:
5'-GTGAATTCCTACTTCTTGTTGACGGCCA-3'

HbR-N:
Forward:
5'-GTGGATCCATGGCCACCCGCGTGAAC-3'

Reverse:
5'-GTGAATTCATCGCCAACCAGGGCACT-3'
```

Finally, respective animals (BALB/c mice and hamsters) were divided into five groups and immunized with endotoxin free indicated plasmid DNA construct. (i.) Unfected control; (ii). Infected control; (iii). Immunized with blank vector (pCDNA3.1) and infected; (iv). immunized with vector containing coding sequence of full length HbR and infected; (v.) immunized with vector containing coding sequence of N-terminal HbR and infected.

Respective animals were immunized by intramuscular injection in the hind thigh using 28-gauge needle with 100 µg of endotoxin-free respective plasmid DNA construct dissolved in sterile saline on day-1 and day-15. On day 27, immunized mice and hamster were challenged with intracardial injection of $1\times10^7$ virulent strain of *Leishmania donovani* (AG83) using 28-gauge needle. Finally, parasite load in spleen and liver from respective animals were determined 60 days after parasite challenge.

Determination of Hepatic and Splenic Parasite Burden in Mice and Hamster

To determine the prophylactic efficacy of HbR vaccination in mice and hamster, animals were sacrificed 60 days after parasite challenge. Liver and spleen from different groups were isolated to determine parasite load. The number of parasite present in the respective organ was determined by microscopic evaluation of Giemsa stained tissue imprints following previously described method (Haldar, et. al., 2009; Mukhopadhyay, et. al., 1989). The parasite burden in respective organs was expressed as Leishman Donovan Unit (LDU), representing the number of amastigotes/1000 host cells X organ weight (Stager, et. al., 2000).

Figure 3A:
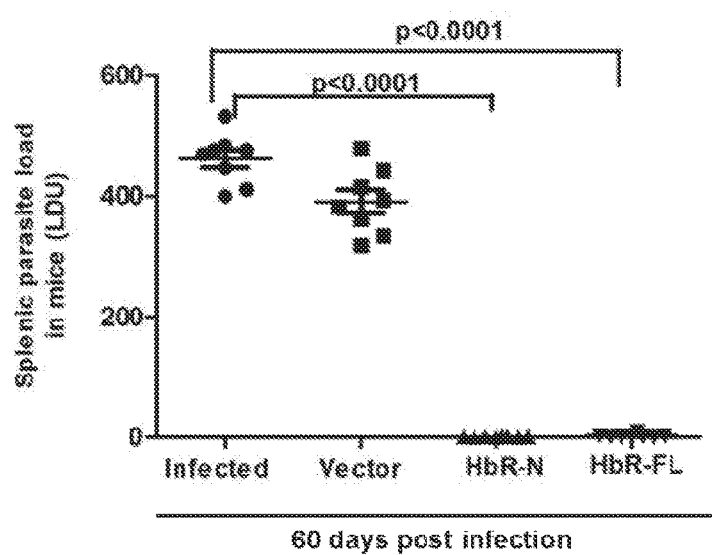
FIGS. 3A, 3B, 3C, 3D, and 3E. HbR-DNA vaccination completely protects animals against challenge of virulent *L. donovani*. BALB/C mice (n=8) or hamster (n=6) were challenged with virulent *Leishmania donovani* after immunization with indicated DNA construct. PBS injected infected animals were used as control. Animals were sacrificed 60 days after infection and parasite load in spleen and liver from respective animals were determined. The results are expressed as LDU±S.E.M. of respective organ in mice and as median values in hamster. Data were analyzed by t test, and levels of significance are indicated by p values.
Figure 3B:
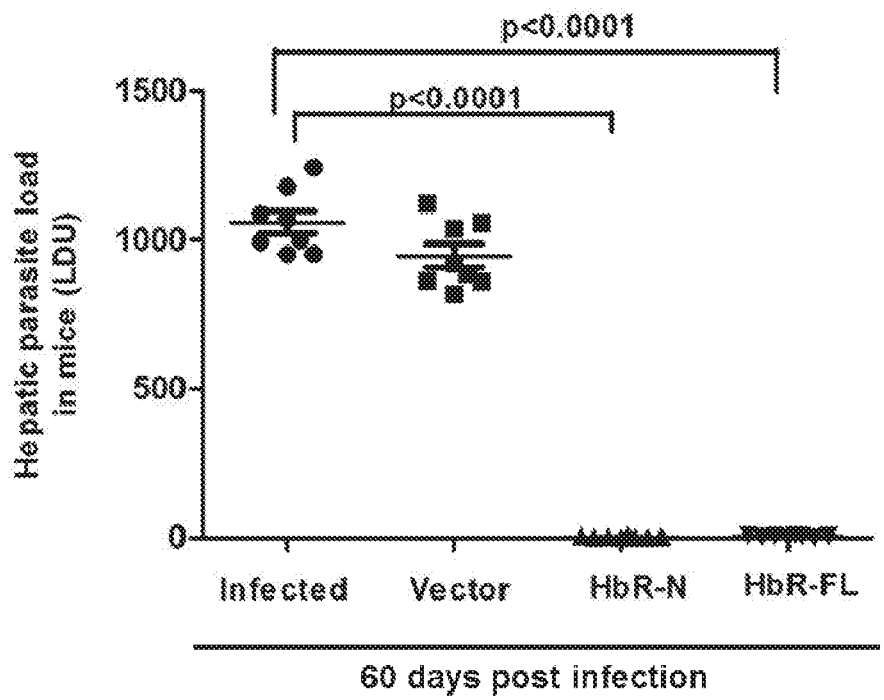
Figure 3C:
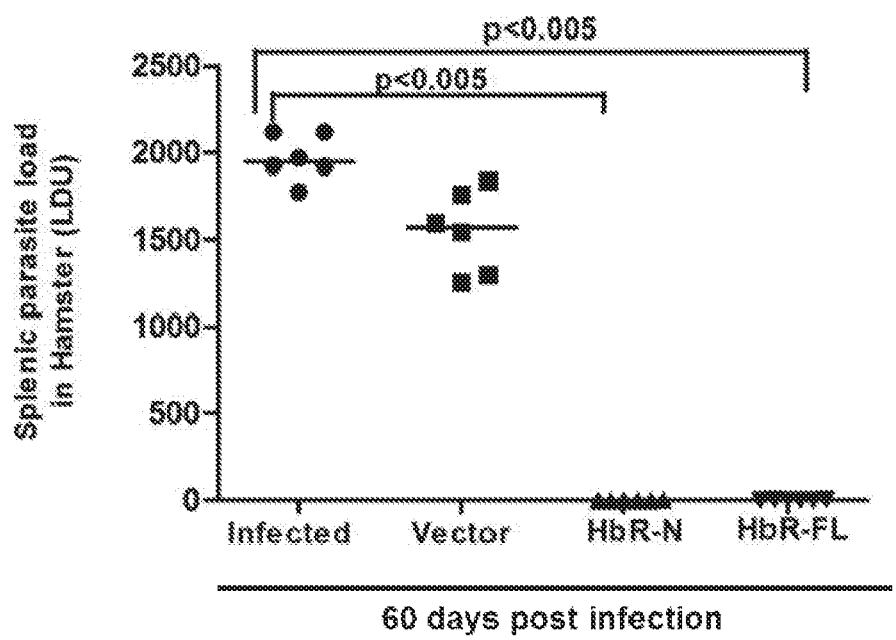
Figure 3D:
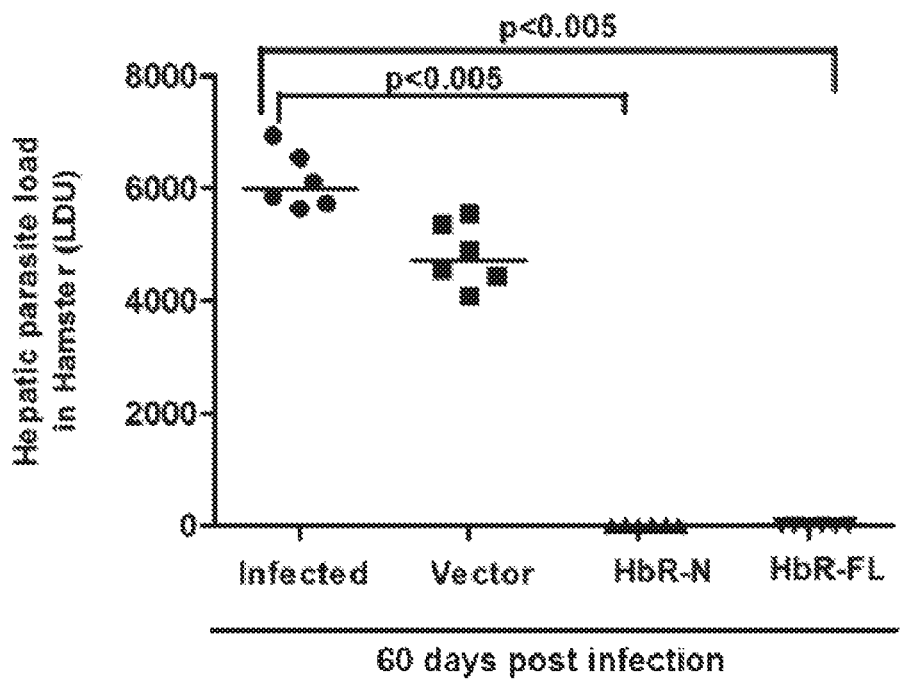
Figure 3E:
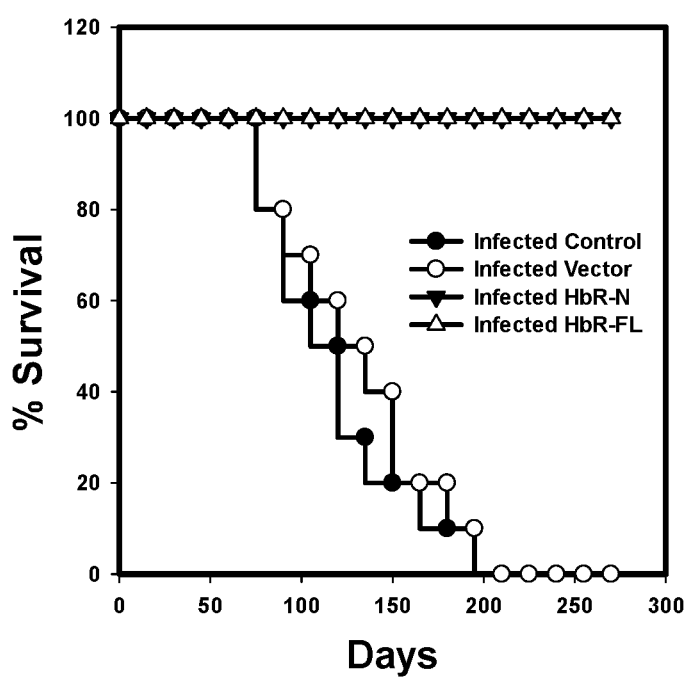

Results obtain in the present innovation showed that immunization of mice with both HbR-N-DNA and HbR-FL-DNA reduce more than 99% of parasite loads in spleen (FIG. 3a) and liver (FIG. 3b) of mice in comparison to unimmunized control mice. No live parasite was detected in the spleen or liver homogenates of most of the mice immunized with HbR-FL or HbR-N indicating complete protection by HbR-DNA vaccination. Similar protection in hamster model of visceral leishmaniasis was also observed. More than 99% of splenic (FIG. 3c) and hepatic (FIG. 3d) parasite load were eliminated by immunizing the hamster with either HbR-FL-DNA or HbR-N-DNA in comparison to control groups. The HbR-FL-DNA or HbR-N-DNA induced sterile protection was supported by the fact that almost all HbR-N-DNA and HbR-FL-DNA vaccinated hamsters were healthy and survived against lethal challenge of virulent *Leishmania* during experimental period of 260 days (FIG. 3e). In contrast, all hamsters from control groups died within 200 days.

Therefore, present innovation demonstrated that immunization of infected animals with HbR-DNA or its part completely protects VL and therefore, HbR or its part is novel vaccine candidate against leishmaniasis. Similar results can be obtained with immunization of HbR or its truncated proteins. As this antigen is conserved among different species of *Leishmania*, therefore, it might be used to protect other forms of leishmaniasis.

Example 4

HbR Vaccination Reversed T-cell Anergy

Cellular immune response is found to be suppressed both in visceral leishmaniasis patient as well as in experimental models. Splenocytes isolated from AG83-challenged HbR-DNA vaccinated animals after 21 days of infection were assayed for T cell proliferation. Briefly, spleens were isolated from different experimental groups of mice and hamster after 21 days of infection and single-cell suspensions of splenocytes were prepared after Ficoll density gradient centrifugation. Cells were resuspended in complete RPMI 1640 and plated in triplicate at a concentration of $1\times10^5$ cells/well in 96-well plate. Subsequently, cells were allowed to proliferate for 3 days at 37° C. in a 5% CO2 incubator either in the presence or absence of HbR protein (5 µg/ml).

Complete soluble antigen from *Leishmania* was used as control. Cells were pulsed with BrDu 2 h before harvesting on day-3 to measure cell proliferation.

Figure 4A:
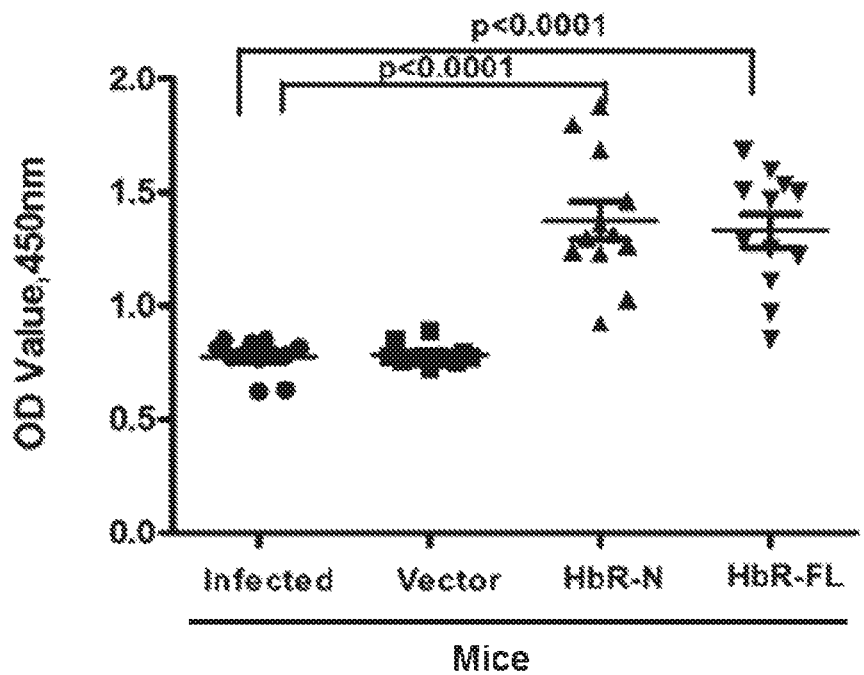
FIGS. 4A, 4B, 4C, and 4D. HbR-DNA vaccination reverses T-cell anergy. Proliferation of splenocytes isolated from indicated group of animals (a,b) were determined in response to HbR. B. Functional significance of splenocyte proliferation in response to indicated antigens was determined by measuring the secretion of IL-2 in the culture supernatant by splenocytes isolated from different groups of mice (c) and hamsters (d) after 48 h of incubation at 37° C. by cytometric bead array.
Figure 4B:
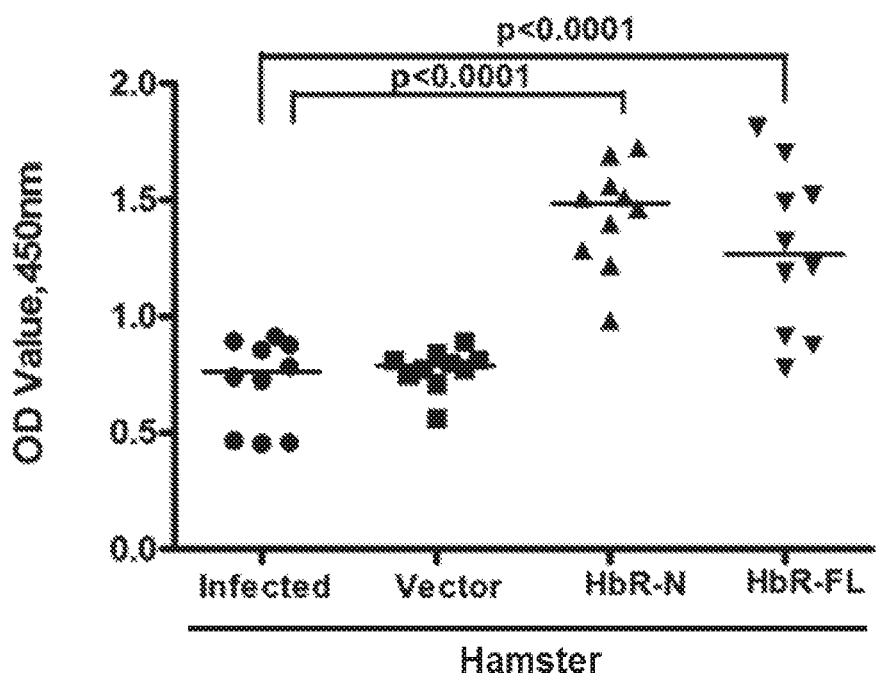
Figure 4C:
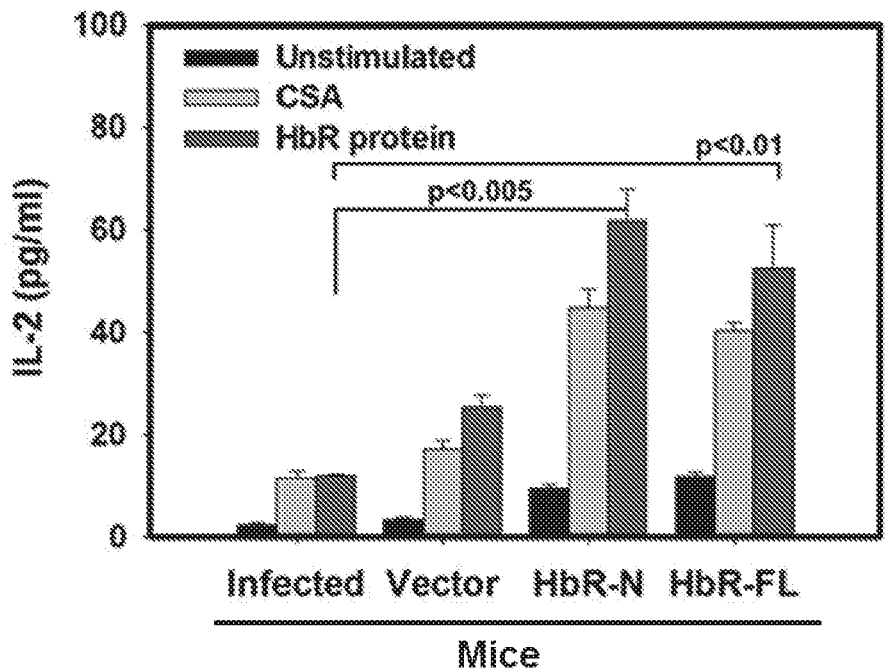
Figure 4D:
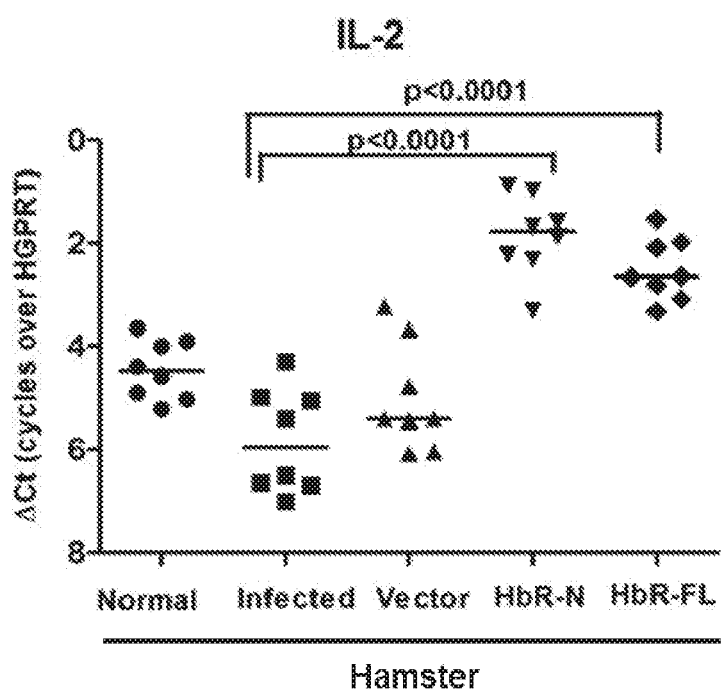
Figure 5A:
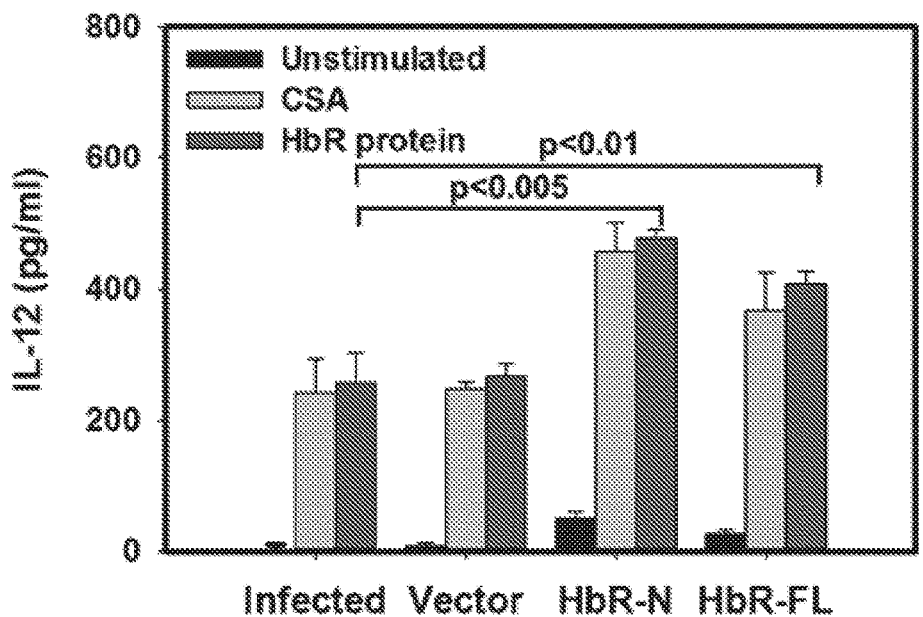
FIGS. 5A, 5B, 5C, 5D, and 5E. HbR vaccination induced Th-1 cytokine in mice. Levels of different cytokine secreted by splenocytes isolated from indicated group of mice in the culture supernatant were measured after 48 h of incubation. a. IL-12; b. IFN-γ; c. TNF-α; d. IL-10; e. IL-4. Results are expressed as mean ±S.D. of pg/ml of cytokines secreted by spenocytes isolated from 12 mice in each group. Results are expressed as mean unit of absorption ±S.D. All data were analyzed by t test, and levels of significance are indicated by p values.
Figure 5B:
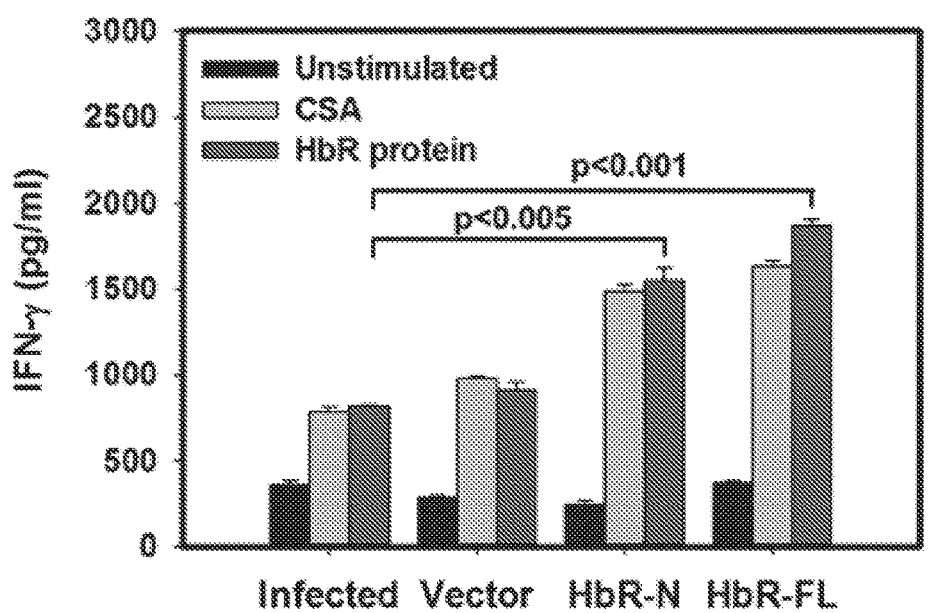
Figure 5C:
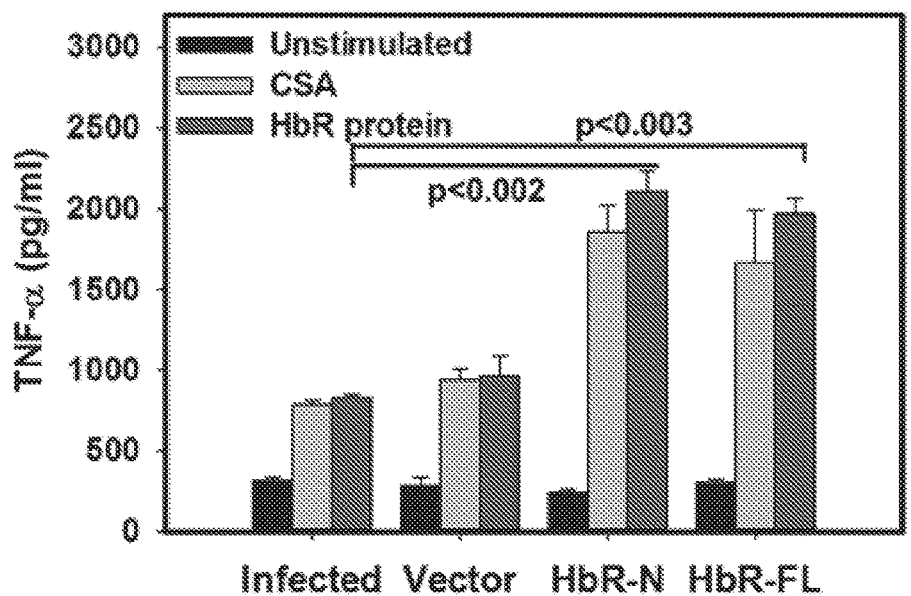
Figure 5D:
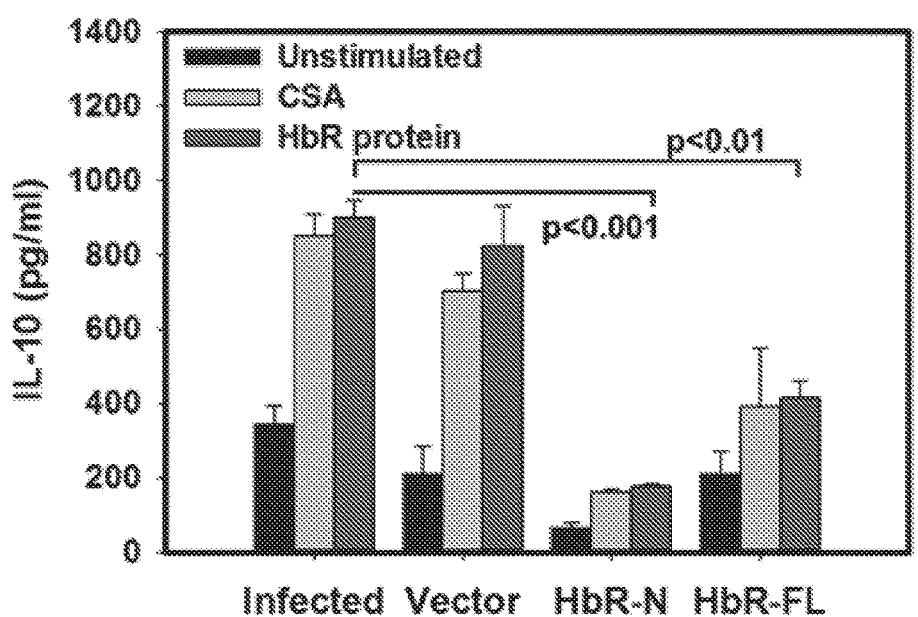
Figure 5E:
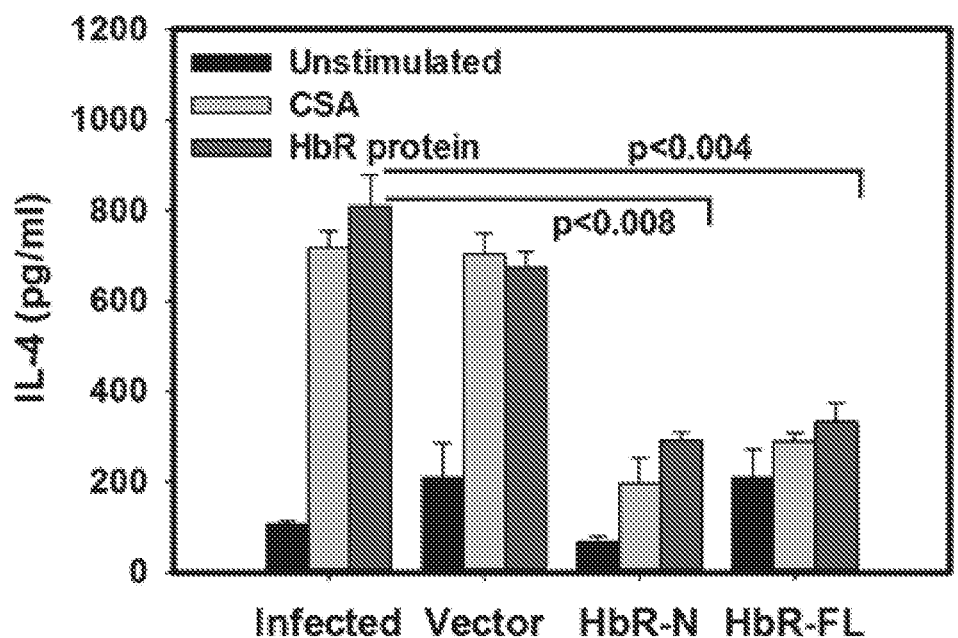
Figure 6A:
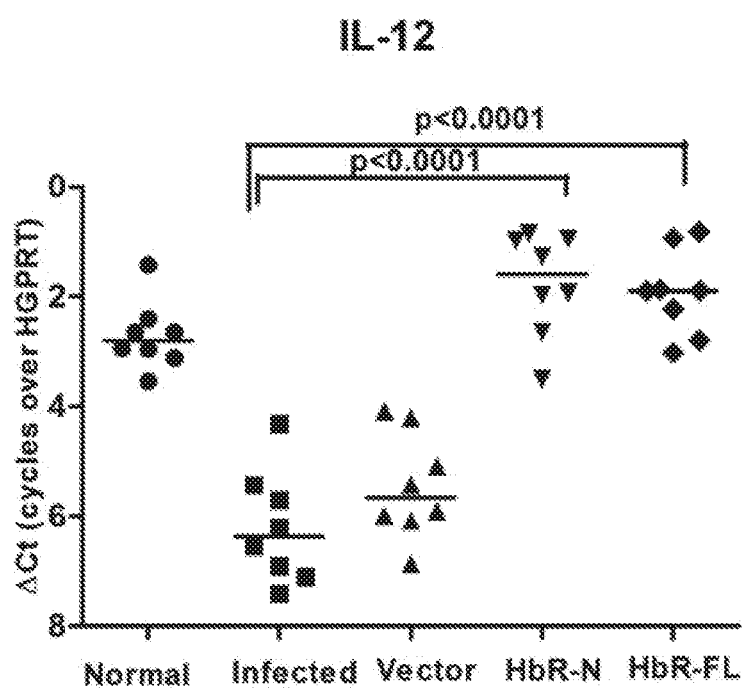
FIGS. 6A, 6B, 6C, 6D, and 6E. HbR vaccination in hamster induced the expression of Th1 cytokines and simultaneously suppressed the expression of disease promoting Th2 cytokines. Levels of different cytokine in splenocytes isolated from indicated group of hamster were measured by Real Time PCR using cytokine specific primers after 48 h of incubation. a. IL-12; b. IFN-γ; c. TNF-α; d. IL-10; e. IL-4. Results are expressed as mean ±S.D. of pg/ml of cytokines secreted by spenocytes isolated from 12 mice in each group. Results are expressed as mean unit of absorption ±S.D. All data were analyzed by t test, and levels of significance are indicated by p values.
Figure 6B:
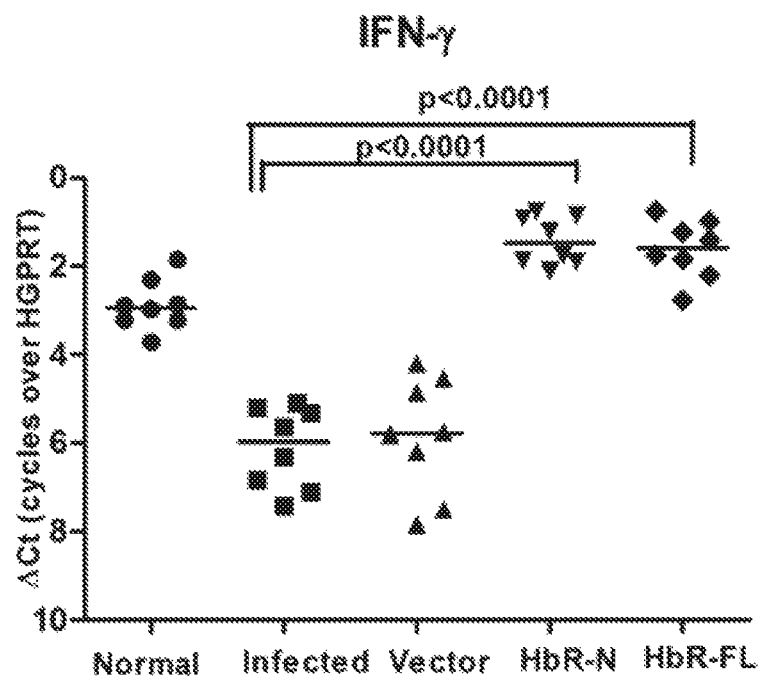
Figure 6C:
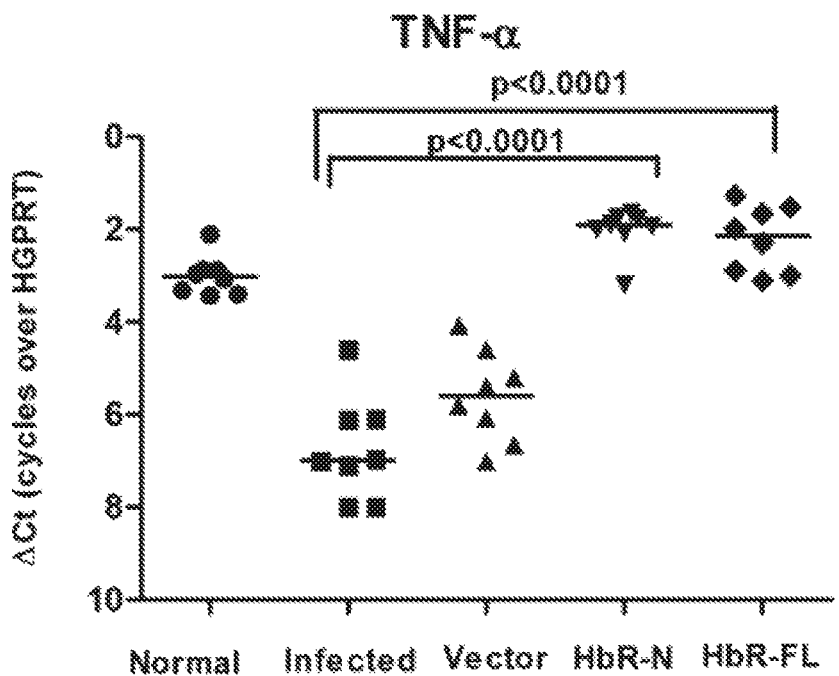
Figure 6D:
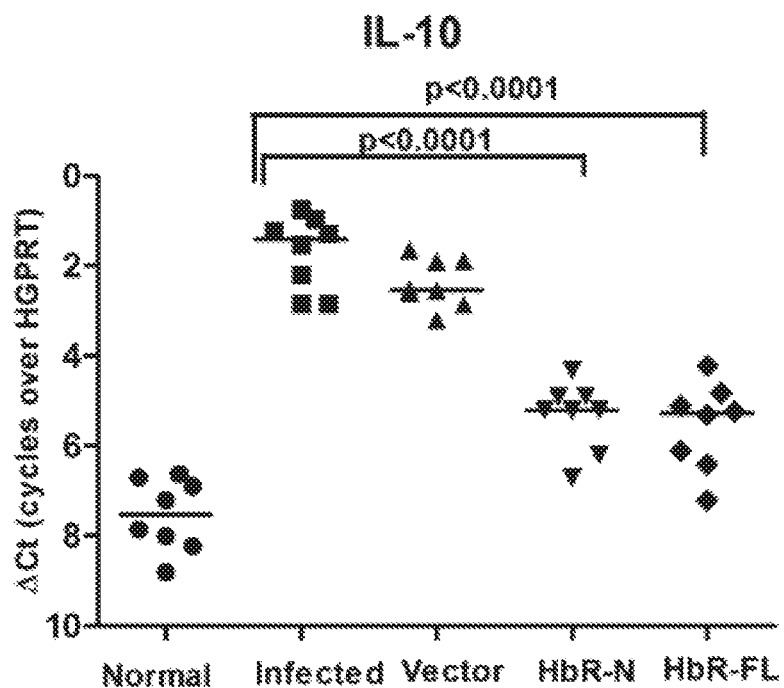
Figure 6E:
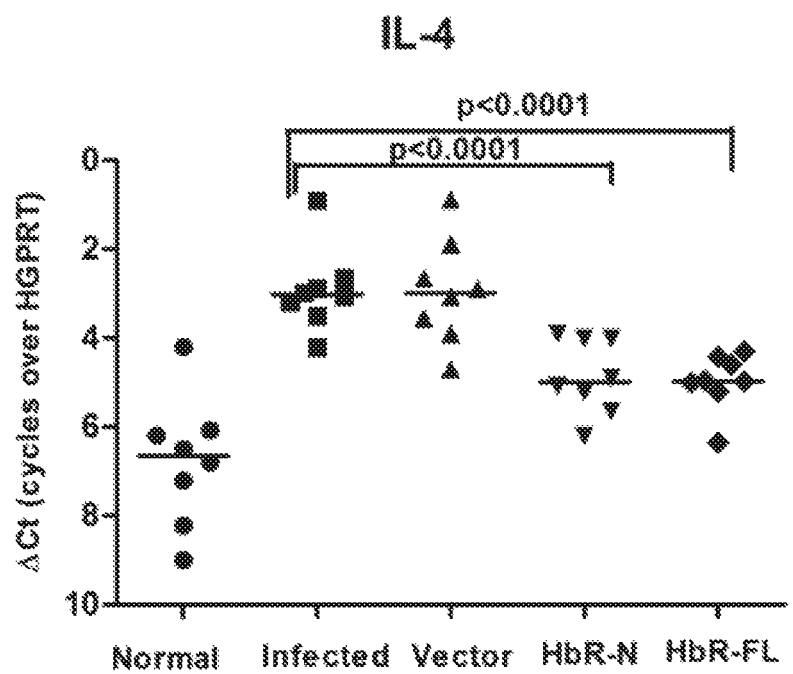

Results obtain in the present innovation showed that HbR-N and HbR-FL DNA immunization significantly enhance the T-cell proliferation in both mice (FIG. 4a) and hamsters (FIG. 4b) in comparison to infected and blank vector-immunized animals in the presence of HbR.

Moreover, depressed splenic T cell response could be due to impaired IL-2 production. To determine the functional significance of induced T-cell proliferation in HbR-DNA vaccinated animals, the levels of IL-2 secretion by spenocytes isolated from different groups of infected mice was measured. Isolated spenocytes from 21 days post-infected mice were stimulated in the presence of 5 μg/ml of HbR protein and culture supernatants were used to measure the levels of IL-2 by ELISA. Results showed that culture supernatants from splenocytes from HbR-FL and HbR-N DNA immunized mice contained about 5 and 6 folds more IL-2, respectively, compared to infected control and vector immunized mice (FIG. 4*c*). Higher levels of IL-2 transcripts in HbR-N and HbR-FL DNA vaccinated infected hamsters was observed in comparison to control animals by real time RT PCR (FIG. 4*d*). These results indicated that full length and N-terminal HbR-DNA vaccination overcome impaired. T-cell proliferation and induce the production of IL-2 to generate appropriate T cell response for parasite clearance.

Example 5

HbR Induced Multifunctional Th-1 Protective Immune Response in Animals

Any vaccine to be successful against VL should skew the immune response towards Th1 type. Thus, the levels of these Th1 cytokines secreted by splenocytes isolated from vaccinated and control groups of animals 21 days after infection was compared by cytometric bead array (CBA). Single-cell suspension of splenocytes from different groups of mice 21 days post-infection was prepared as described previously. Subsequently, $2.5\times10^5$- cells/well in complete RPMI 1640 medium were plated in 96 well plates and incubated for 48 h at 37° C. in 5% $CO_2$ incubator in the presence or absence of 5 ug/ml of indicated proteins. After 48 h culture supernatant were collected by centrifugation. Levels of different cytokine in the culture supernatant were measured by cytometric bead array (multiplexing). Mouse Th1/Th2 and Mouse Inflammatory kit (BD Biosciences) were used for cytometric Bead Array (CBA). All the data were analyzed using Fcap Array in a FACS ARIAII Flow Cytometer (BD).

The results presented in the current innovation show that spenocytes isolated from HbR-FL-DNA immunized mice in response to HbR protein induce about 2.27 folds increase in IFN-γ production, 2 folds increase in IL-12 and 2.37 folds increase in TNF-α production whereas cells from HbR-N-DNA vaccinated mice produced about 1.88, 2 and 2.69 folds more IFN-γ, IL-12 and TNF-α, respectively, compared to that of infected and vector control groups (FIG. 5*a-c*). In contrast, vaccination with HbR-FL-DNA and HbR-N-DNA suppressed about 2.15 and 5 folds less production of Th1 suppresive cytokine IL-10, respectively, compared to that of infected controls (FIG. 5*d*). In addition, HbR-FL-DNA and HbR-N-DNA vaccination resulted in 2.42 and 2.77 folds decrease in production of Th2 signature cytokine IL-4, respectively, in comparison to control groups (FIG. 5*e*). These results indicated that full length and N-terminal HbR-DNA vaccination induce TH1 protective response. Interestingly, significantly more amount of IL-12 and higher IFN-γ/IL-10 ratio were obtained in HbR-N-DNA than HbR-FL-DNA vaccination, indicating greater Th1 bias protective immune response generated by HbR-N-DNA.

Example 6

Measurement of mRNA Levels of Different Cytokines in Splenocytes Isolated from Hamster by Real-time PCR Splenocytes were isolated from 8 randomly chosen animals from different group of hamsters. Total RNA was isolated using Trizol reagent (Invitrogen) and used for cDNA synthesis of using maxima first-strand cDNA synthesis kit (Fermentas). Real Time PCR was performed following the method described earlier using cytokine specific primers. Briefly, it was carried out with 12.5 μl of SYBR green PCR master mix (ABI), 2 μl of cDNA from RT reaction mix, and gene specific primers in a final volume of 25 μl. PCR was conducted under the following conditions: initial denaturation at 95° C. for 2 min followed by 40 cycles, each consisting of denaturation at 95° C. for 30 s, annealing at 55° C. for 40 s, and extension at 72° C. for 40 s per cycle using the ABI 7500 Real time PCR system. All quantifications were normalized to the housekeeping gene HGPRT. A no-template control cDNA was included to eliminate contaminations. Differences in gene expression were calculated by the comparative CT method. Results are expressed as the degrees of difference between ΔCT values of test and comparator samples.

Transcript profiles of different cytokines in splenocytes isolated from vaccinated and control hamsters after 21 days of infection was compared by RT-PCR. Results also showed that levels of IFN-γ, IL-12 and TNF-α transcript are up-regulated whereas IL-10 expression is lower in the vaccinated hamsters in comparison to control groups. No significant change was observed in IL-4 expression between different groups of hamster (FIG. 6*a-e*). Thus, HbR-DNA vaccination not only induced protective Th1 response but also suppressed disease promoting cytokines like IL-10 and IL-4, to achieve complete protection both in mice and hamster models of VL.

Example 7

Determination of HbR Specific IgG1 and IgG2 Antibody Response in HbR-DNA Vaccinated Mice and Hamster To determine the levels of anti-HbR specific IgG1 and IgG2a antibody in vaccinated and control groups of animals, blood was collected on 21 days post-infection and sera samples were analyzed for the presence of HbR-specific antibody. The 96-well ELISA plates (BD) were coated with full-length HbR protein (2 µg/ml) in PBS overnight at 4° C. Plates were washed and blocked with 5% FCS in PBS at room temperature for 1 h to prevent nonspecific binding. Sera (1:10 dilution) from different groups of mice was added into HbR-coated wells and incubated for 2 h at room temperature. Well were washed and incubated with biotin-conjugated Rat anti-mouse IgG for 1 h at room temperature followed by another 1 h incubation with avidin-conjugated HRP. ABTS as peroxidase substrate in citrate buffer (0.1 M, pH 4.3) with 0.1% H2O2 was added and absorbance was read on ELISA plate reader at 405 nm. Similar assay using biotin-conjugated mouse anti-hamster IgG1 and mouse anti-Armenian and anti-Syrian hamster IgG2 was carried out to detect the levels of HbR specific IgG1 and IgG2 levels in hamster sera.

Figure 7A:
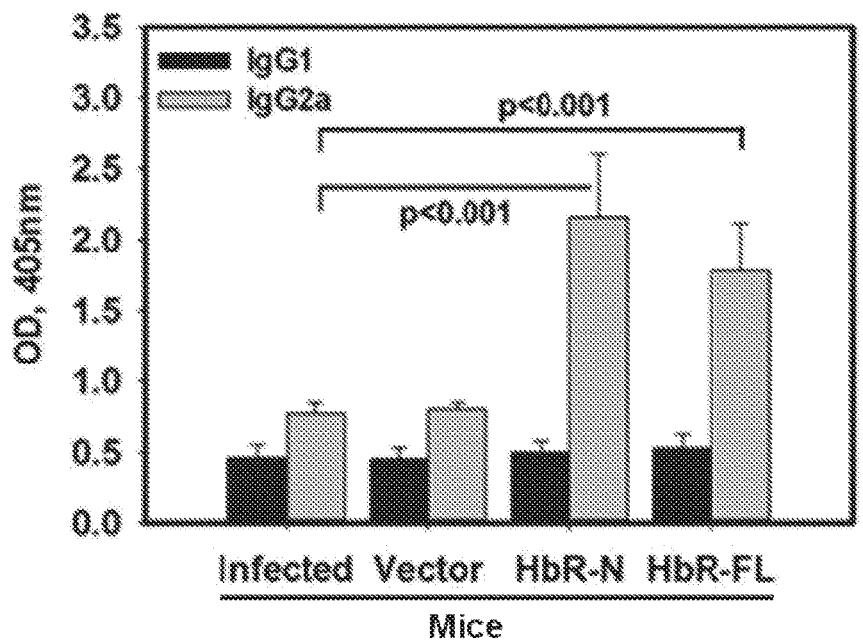
FIGS. 7A and 7B. Determination of HbR specific antibody in vaccinated and control groups of mice (a) and hamster (b). Bloods was collected from vaccinated and control groups of indicated animals and serum was analyzed for the presence of HbR-specific antibody by ELISA. Results are expressed as mean unit of absorption ±S.D. All data were analyzed by t test, and levels of significance are indicated by p values.
Figure 7B:
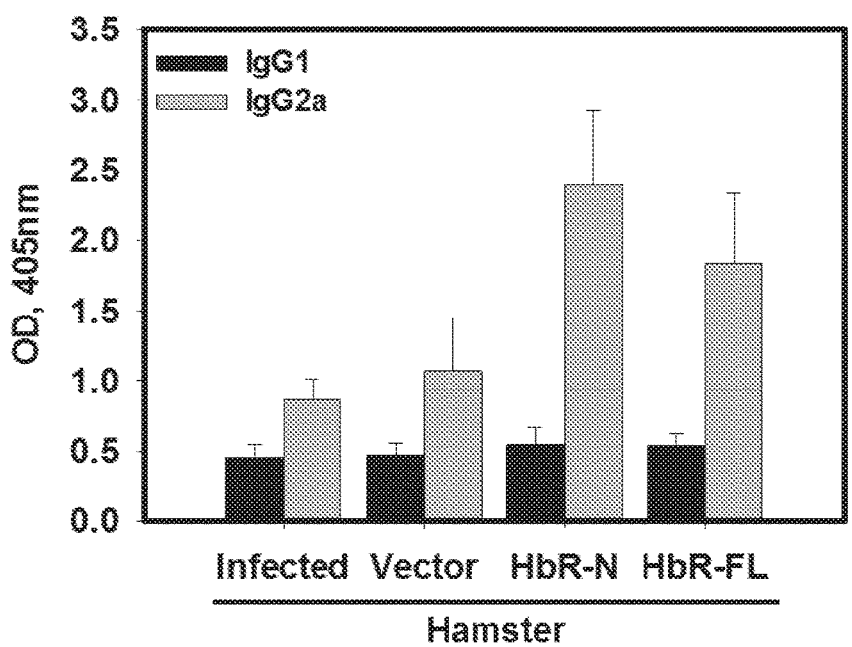
Figure 8:
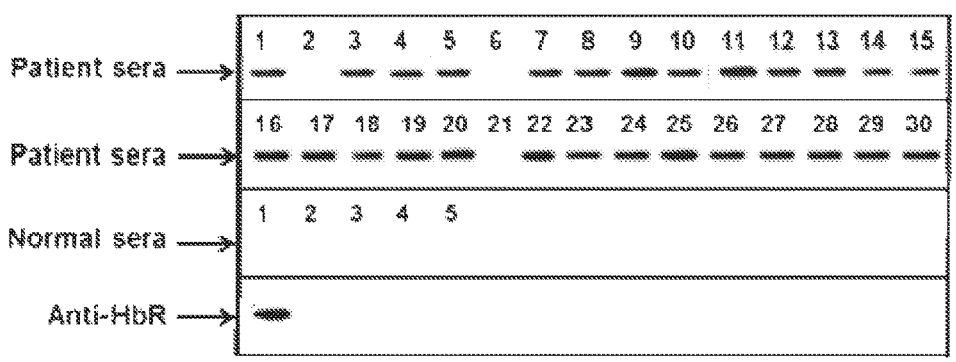
FIG. 8. Detection of anti-HbR antibody in kala-azar patient serum.

These results showed that immunization of HbR-FL and HbR-N DNA generated about 3-4 folds higher IgG2a levels vaccinated mice (FIG. 7a) and hamster (FIG. 7b) compared to controls Higher level of IgG2a should trigger pathogen protection in vaccinated animals. Thus, HbR-DNA vaccination induced both humoral and cell-mediated immune response.

HbR Vaccination Induces both CD4$^+$ and Cytotoxic CD8$^+$ T-cells Response

Generation of multifunctional CD4$^+$ T-cells response by vaccination was found to induce better protection (Darrah, et. al., 2007). Multiparameter flow cytometry analysis revealed that HbR-DNAs vaccination generated significantly higher population of both CD4$^+$ and cytotoxic CD8$^+$ T-cells with very high levels of single positive cytokines like IFN-$\gamma^+$, TNF-$\alpha^+$ and IL-2$^+$ compared to infected controls (data not shown). IFN-$\gamma$ was shown to mediate pathogen killing (Cooper, et. al., 1993; Flynn, et. al., 1993) and the effect was additive by TNF-$\alpha$ (Liew, et. al., 1990), thus, enhanced production IFN-$\gamma^+$TNF-$\alpha^+$ CD4$^+$ and CD8$^+$ T-cells by HbR-DNA vaccination rendered better protection against VL. Similarly, higher frequency of antigen specific IFN-$\gamma^+$IL-2$^+$ CD4$^+$ T-cells by HbR-DNA immunization might provide durable protection by developing memory cells (Wu, et. al., 2002) in comparison to IFN-$\gamma$ or IL-2 alone. IL-12 was reported as strong-Th1-inducing adjuvant (Heinzel, et. al., 1993; Sypek, et. al., 1993) and also enhanced targeting intracellular pathogens to lysosome (Bhattacharya, et. al., 2006). Thus, increased levels of IL-12 in HbR-DNA vaccinated animals contributed to parasite clearance. Taken together, the sterile protection observed in the present innovation by HbR-DNA vaccination in animals is due to simultaneous activation of both CD4$^+$-Th1 and cytotoxic CD8$^+$ T-cell response of immune system.

Example 8

HbR as Diagnostic Marker

To evaluate, HbR as potential marker for diagnosis of *Leishmania*, HbR was purified from *Leishmania* as described previously. Confirmed kala-azar patient sera were used with approval of the human ethics committee from Rajendra Memorial Research Institute of Medical Sciences, Patna, India. Purified HbR protein (1 µg) was subjected to SDS-PAGE, transferred onto nitrocellulose membrane and incubated with appropriate dilution of patient sera. Normal sera prepared from healthy individuals were used as control. Membranes were washed and probed with anti-human IgG+IgM antibody conjugated with HRP.

Interestingly, we found that 27 out of 30 VL patient sera possess antibody-against HbR demonstrating that HbR is a potential candidate for developing a diagnostic procedure for *Leishmania*.

REFERENCES

1. Bacellar, O., D'oliveira, A. Jr., Jerônimo, S. & Carvalho, E. M. IL-10 and IL-12 are the main regulatory cytokines in visceral leishmaniasis. *Cytokine* 12, 1228-1231 (2000).
2. Bhattacharya, M., Ojha, N., Solanki, S., Mukhopadhyay, C. K., Madan, R., Patel, N., Krishnamurthy, G., Kumar, S., Basu, S. K. & Mukhopadhyay A. IL-6 and IL-12 specifically regulate the expression of Rab5 and Rab7 via distinct signaling pathways. *EMBO J.* 25, 2878-2888 (2006).
3. Cooper, A. M. et al. Disseminated tuberculosis in interferon γ gene-disrupted mice. *J. Exp. Med.* 178, 2243-2247 (1993).
4. Croft, S. L. & Coombs, G. H. Leishmaniasis-current chemotherapy and recent advances in the search for novel drugs. *Trends. Parasitol.* 19, 502-508 (2003).
5. Darrah, P. A., Patel, D. T., Luca, P. M. D., Lindsay, R. W. B., Davey, D. F., Flynn, B. J., Hoff, S. T., Andersen, P., Reed, S. G., Morris, S. L., Roederer, M., & Seder, R. A. Multifunctional TH1 cells define a correlate of vaccine-mediated protection against *Leishmania major*. *Nat. Med.* 13, 843-850 (2007).
6. Flynn, J. L. et al. An essential role for interferon γ in resistance to Mycobacterium, tuberculosis infection. *J. Exp. Med.* 178, 2249-2254 (1993).
7. Heinzel, F. P., Schoenhaut, D. S., Rerko, R. M., Rosser, L. E. & Gately, M. K. Recombinant interleukin 12 cures mice infected with *Leishmania major*. *J. Exp. Med.* 177, 1505-1509 (1993).

8. Haldar, A. K., Banerjee, S., Naskar, K., Kalita, D., Islam, N. S. & Roy, S. Sub-optimal dose of Sodium Antimony Gluconate (SAG)-diperoxovanadate combination clears organ parasites from BALB/c mice infected with antimony resistant *Leishmania donovani* by expanding antileishmanial T-cell repertoire and increasing IFN-γ to IL-10 ratio. *Exp. Parasitol.* 122, 145-154 (2009).

9. Kelly, J. X., Ignatushchenko, M. V., Bouwer, H. G., Peyton, D. H., Hinrichs, D. J., Winter, R. W. & Riscoe, M. Antileishmanial drug development: exploitation of parasite heme dependency. *Mol. Biochem. Parasitol.* 126, 43-49 (2003).

10. Krishnamurthy, G., Vikram, R., Singh, S. B., Patel, N., Agarwal, S., Mukhopadhyay, G., Basu, S. K. & Mukhopadhyay, A. Hemoglobin receptor in *Leishmania* is a hexokinase located in the flagellar pocket. *J. Biol. Chem.* 280, 5884-5891 (2005).

11. Kedzierski, L., Sakthianandeswaren, A., Curtis, J. M., Andrews, P. C., Junk, P. C. & Kedzierska, K. Leishmaniasis: current treatment and prospects for new drugs and vaccines. *Curr. Med. Chem.* 16, 599-614 (2009).

12. Kedzierski, L. Leishmaniasis vaccine: Where are we today? *J. Global. Infect. Dis.* 2, 177-185 (2010).

13. Liew, F. Y., Li, Y. & Millott, S. Tumor necrosis factor-alpha synergizes with IFN-gamma in mediating killing of *Leishmania* major through the induction of nitric oxide. *J. Immunol.* 145, 4306-4310 (1990).

14. Mukhopadhyay, A., Chaudhuri, G., Arora, S., Sehgal, S. & Basu, S. K. Receptor-mediated drug delivery to macrophages in chemotherapy of Leishmaniasis. *Science* 244, 705-707 (1989).

15. Nylen, S. & Sacks, D. Interleukin-10 and the pathogenesis of human visceral leishmaniasis. *Trends Immunol* 28, 378-384 (2007).

16. Patel, N., Singh, S. B., Basu S. K. & Mukhopadhyay, A. *Leishmania* requires Rab7-mediated degradation of endocytosed hemoglobin for their growth. *Proc. Natl. Acad. Sci. USA.* 105, 3980-3985 (2008).

17. Sypek, J. P., Chung, C. L., Mayor, S. E., Subramanyam, J. M., Goldman, S. J., Sieburth, D. S. et al. Resolution of cutaneous leishmaniasis: interleukin 12 initiates a protective T helper type 1 immune response. *J. Exp. Med.* 177, 1797-802 (1993).

18. Sengupta, S., Tripathi, J., Tandon, R., Raje, M., Roy, R. P., Basu S. K. & Mukhopadhyay, A. Hb endocytosis in *Leishmania* is mediated through a 46-kDa protein located in the flagellar pocket. *J. Biol. Chem.* 274, 2758-2765 (1999).

19. Stager, S., Smith, D. F. & Kaye, P. M. Immunization with a recombinant stage-regulated surface protein from *Leishmania donovani* induces protection against visceral leishmaniasis. J. Immunol. 165, 7064-7071 (2000).

20. Sah J F, Ito H, Kolli B K, Peterson D A, Sassa S, Chang K. P. Genetic rescue of *Leishmania* deficiency in porphyrin biosynthesis creates mutants suitable for analysis of cellular events in uroporphyria and for photodynamic therapy. *J. Biol. Chem.* 277: 14902,-14909 (2002).

21. Singh, S. B., Tandon, R., Krishnamurthy, G., Vikram, R., Sharma, N., Basu S. K. & Mukhopadhyay, A. Rab5 mediated endosome-endosome fusion regulates hemoglobin endocytosis in *Leishmania donovani. EMBO J.* 22, 5712-5722 (2003).

22. Singh, B. & Sundar, S. Leishmaniasis: Vaccine candidates and perspectives. *Vaccine* 30, 3834-3842 (2012).

23. Wu, C. Y. et al. Distinct lineages of TH1 cells have differential capacities for memory cell generation in vivo. *Nat. Immunol.* 3, 852-858 (2002).

24. World Health Organization (WHO). Parasitic diseases: Initiative for Vaccine Research.Available:http://www.who.int/vaccine_research/diseases/soa_parasitic/en/index 4.html (2012).

---

The invention claimed is:

1. A GST HbR-DNA for eliciting an immune response against virulent *Leishmania*, wherein said GST HbR-DNA comprises GST and a nucleotide sequence selected from the group consisting of: a) nucleotide sequence as set forth in any one of SEQ ID NO: 1 (HbR-FL), SEQ ID NO: 2 (HbR-N) or fragments thereof; and b) a nucleotide sequence that encodes polypeptide having amino acid sequence as set forth in SEQ ID NO: 3.

2. The GST-HbR DNA as claimed in claim 1, wherein the said HbR-DNA consists of nucleotide sequence as set forth in SEQ ID NO: 2 (HbR-N).

3. A recombinant DNA vector comprising the DNA as claimed in claim 1 operably linked to a promoter.

* * * * *